United States Patent [19]

Woods et al.

[11] 4,279,995

[45] Jul. 21, 1981

[54] SELECTIVE SALMONELLA CARBOHYDRATE AND MEDIUM CONSTRUCTED THEREFROM

[75] Inventors: Leodis V. Woods, St. Louis; Paul Stassi, Hazelwood; Ralph A. Wilkinson, Florissant, all of Mo.

[73] Assignee: McDonnell Douglas Corporation, Long Beach, Calif.

[21] Appl. No.: 99,649

[22] Filed: Dec. 3, 1979

[51] Int. Cl.³ .............................................. C12Q 1/10
[52] U.S. Cl. ...................................... 435/38; 435/253
[58] Field of Search ....................... 435/34, 35, 36, 37, 435/38, 39, 40, 243, 244, 253

[56] References Cited

U.S. PATENT DOCUMENTS

| 4,072,571 | 2/1978 | Gibson et al. | 435/38 |
| 4,072,572 | 2/1978 | Lanham et al. | 435/38 |
| 4,072,575 | 2/1978 | Lanham et al. | 435/38 |

*Primary Examiner*—Robert J. Warden
*Attorney, Agent, or Firm*—George W. Finch; Walter J. Jason; Donald L. Royer

[57] ABSTRACT

2-Deoxy-D-Ribose is used as a carbohydrate source which selectively differentiates all of the Salmonella spp., Arizona spp., and 60% of the *Citrobacter freundii* from other members of the Enterobacteriaceae family. By combining the 2-Deoxy-D-Ribose with *Citrobacter freundii* inhibitors and thioglycollic acid, sodium salt to impart semi-anaerobic conditions in the medium as well as suitable nutrients and buffers, a selective Salmonella broth is compounded which lends itself to automated identification or enumeration systems.

13 Claims, No Drawings

SELECTIVE SALMONELLA CARBOHYDRATE AND MEDIUM CONSTRUCTED THEREFROM

CROSS REFERENCE TO RELATED PATENTS

The present invention can be used with the optical detection systems disclosed in U.S. Pat. No. 3,963,355 entitled, "Process and Apparatus for Analyzing Specimens for the Presence of Microorganisms Therein;" U.S. Pat. No. 4,118,280 entitled, "Automated Microbial Analyzer;" U.S. Pat. No. 4,116,775 entitled, "Machine and Process for Reading Cards Containing Medical Specimens;" and U.S. Pat. No. 4,062,876 entitled, "Sensitive PH Indicator." The information therein is incorporated by reference as though fully set forth herein below.

BACKGROUND OF THE INVENTION

The patents referenced above describe mechanisms and apparatus suitable for analyzing specimens for specific microorganisms utilizing a plastic tray or card which contains a plurality of dried culture media specific to a single genus or species of organism. The dried media are contained in separate cells in the card which are connected by a network of passageways to a filling port. When a fluid sample is inserted into the card, mixed with media in the cells, and incubated, the organisms present in the specimen interact with the specific culture media. The interaction of the specimen and the specific culture media produces characteristic optical changes in the contents of the cell which are read to indicate presence of the organisms. The optical change in each cell involves a change in light transmitting properties thereof either through a color change or a change in turbidity. The optical change usually is caused by the metabolic activity of the organism which, for example, may produce an acid which changes the color of a pH sensitive indicator in the media. The change and the light transmitting properties of the medium also can be caused by a precipitate forming in the medium due to metabolic activity of the organism or by the mass of growing colonies of the organism. The metabolically caused changes generally yield considerably earlier results than do growth caused changes. The specific media designed for use in the cards of the aforesaid system all are designed to favor growth of one genus or species of microorganism and to inhibit growth of other organisms. The media are capable of being freeze dried and they are formulated to function in the low oxygen environment of the cells of the card described in detail in the above referenced patents.

Salmonella spp. are microorganisms which are pathogenic to the human body. The presence of these microorganisms in the urine, feces, or blood of the human body is a reliable indication of bacterial infection in the body. Salmonella can be introduced into a human body through contaminated food and water. Therefore, it is desirable to detect, identify and enumerate Salmonella in the effluent from sewage treatment plants, in food produced by food processing plants, meat packaging plants and hospitals to insure the wholesomeness of products intended for consumption by humans. The above concerns also apply as well to animals other than humans.

Heretofore, media which could selectively isolate Salmonella in pure cultures of the bacteria have included Salmonella Shigella Agar, Bismuth Sulfite Agar and XLD Agar all produced by BBL (Baltimore Biological Laboratory) and the HEA formulation disclosed in the text, "Manual of Clinical Microbiology," 2nd Edition. All rely on the non-utilization of certain carbohydrates and therefore produce unwanted false positives especially in mixed culture media for use in machines as described in the patents referenced above.

SUMMARY OF THE INVENTION

This invention involves a selective carbohydrate and a medium for detection of Salmonella. It has been discovered that 2-Deoxy-D-Ribose when used as a carbohydrate source will selectively differentiate all of the Salmonella spp., Arizona spp. and 60% of the *Citrobacter freundii* from other members of the Enterobacteriaceae family. Of that group, only Salmonella-Arizona and some *Citrobacter freundii* can utilize the carbohydrate therein for their metabolic processes. Therefore, its use would be highly effective in many media wherein it is desired to selectively cultivate Salmonella-Arizona. The carbohydrate could be incorporated into a medium which would be compatible with the above discussed Automated Microbial Identification System. When formulated for use with assorted specimens, the medium contains in addition to the 2-Deoxy-D-Ribose suitable protein, bile salts, thioglycollic acid (sodium salt), dipotassium phosphate, reduced aniline blue, sodium chloride, ascorbic acid, ferric ammonium citrate, sodium thiosulfate and P-Bromobenzoic acid. The proper mixture of such ingredients results in a medium which can selectively identify the Salmonella in the controlled oxygen micro-environment of the identification system described above.

It is therefore an object of the present invention to provide a selective carbohydrate for Salmonella-Arizona which is readily available commercially.

It is another object to provide an improved selective medium for Salmonella spp. which can operate in the presence of competing organisms within the environment of the identification card of an automated microbial analyzer.

Another object is to provide a Salmonella spp. identification media which can perform the desired function in a controlled oxygen micro-environment.

Another object is to provide a quick acting Salmonella spp. identification media.

Another object is to provide a selective medium for Salmonella spp. which rarely produces false positives.

These and other objects and advantages of the present invention will be come apparent to those skilled in the art after considering the following detailed specification in which the selective carbohydrate and a preferred basic formulation of the medium is disclosed.

DETAILED DESCRIPTION OF THE PRESENT INVENTION

The detection broth medium of the present invention contains from 0.1–1.0 g % of 2-Deoxy-D-Ribose as the carbohydrate source which selectively allows the growth of Salmonella spp., Arizona spp., and some *Citrobacter freundii* to the exclusion of all other Enterobacteriaceae. The 2-Deoxy-D-Ribose is available from Calbiochem-Behring Corporation and is described on page 330 of their Catalog No. 2610. Merck describes it as D-2-Deoxyribose, Desoxyribose, D-2-deoxyarabinose, D-2-ribodesose, D-erythro-2-deoxypentose or thyminose with a formulation of $C_5H_{10}O_4$ and a mol weight of 134.13. C 44.77%, H 7.5%, O 47.71%. It is prepared by isolation from deoxyribonucleic acid by acidic hydrolysis of purine deoxyribonucleosides which have been isolated by ion-exchange resin chromatography.

Protein from 0.05–2.0 g % is incorporated into the medium to allow for the growth of the Salmonella spp. once they have established an energy source from the carbohydrate 2-Deoxy-D-Ribose. Any protein source will work but Proteose Peptone #3 from Difco seems to work best in the present formulations. A typical analysis of Proteose Peptone #3 is Ash 5%, Total Nitrogen 13%, Amino Nitrogen 3%, with Amino acids (in percentages) of Arginine 6%, Aspartic Acid 6.5%, Glutamic Acid 11.0%, Histidine 2.0%, Glycine 9.0%, Isoleucine 3.5%, Leucine 6.0%, Lysine 5.0%, Methionine 2.0%, Phenylalanine 3.0%, Threonine 3.0%, Tyrosine 0.5%, Valine 4.0% and with Vitamin Factors (micrograms per gram) of Pyridoxine 4.0, Biotin 0.2, Thiamine 3.0, Nicotinic Acid 169.0 and Riboflavin 13.0. Bile salts in the amount of 0.05–1.0 g % is used in the medium both as a pH indicator and an inhibitor. As a pH indicator it forms a precipitate as the pH of the medium goes down due to the metabolism by the Salmonella spp. of the carbohydrate. As an inhibitor it slows down or stops the growth of gram positive organisms. Other bile salts may work, however, of the ones tried in the present formulation, Bile Salts Mixture from BBL seems to give the best results. Bile Salts Mixture contains bile extractives and is a mixture of surfactants which inhibit gram positive organisms such as bacillus species. Bile Salts Mixture is a commercially available material commonly used in media to inhibit gram positive organisms. Beef extract in the amount of 0.01–0.5 g %, ferric ammonium citrate in the amount of 0.005–0.1 g %, and sodium thiosulfate in the amount of 0.005–2 g % are incorporated into the medium to improve and speed up the growth of Salmonella spp. Thioglycollic acid (sodium salt), in the amount of 0.01–0.6 g % is used in the medium to impart semi-anaerobic conditions to the medium which seems to allow better acid production by the Salmonella spp. and to slow down acid production by *Citrobacter freundii*. Dipotassium phosphate in the amount of 0.0–1.0 g % is used in the medium to buffer the pH and prevent small erratic pH changes which might be due to conditions other than carbohydrate metabolism. Reduced aniline blue, 1% solution in the amount of 0.5–5 ml % as described in U.S. Pat. No. 4,062,876 is used as a pH indicator. It changes from straw colored at pH 6.8–7.2 to blue at pH 6.5 or lower. Other pH indicators can and have been used but the reduced aniline blue is fully compatible with the optics of the automated microbial analyzer and therefore is preferred in this particular application. Sodium chloride up to 1.0 g % can be used in the medium to create a more isotonic solution which will enhance the growth of positive organisms. Ascorbic acid in the amount of 0.01–0.4 g % is used as a *Citrobacter freundii* inhibitor and P-Bromabenzoic acid in the amount of 0.004–0.08 g % is also used as a *Citrobacter freundii* inhibitor. These inhibitors (ascorbic acid and P-Bromobenzoic acid) also eliminate Arizona positives. An actual formulation for use in the Automated Microbial Monitor is as follows:

| | |
|---|---|
| Water (Distilled) | 95.0 ml |
| pH to 6.8–7.5 | |
| 2-Deoxy-D-Ribose | .5 g |
| Proteose Peptone #3 | .5 g |
| Bile Salt Mix | .5 g |

| -continued | |
|---|---|
| Thioglycollic acid, sodium salt | .3 g |
| Dipotassium phosphate | .1 g |
| Sodium chloride | .5 g |
| Beef extract | .1 g |
| Ferric ammonium citrate | .04 g |
| Sodium thiosulfate | .05 g |
| Reduced aniline blue | 2.00 ml |
| Ascorbic acid | .3 g |
| P-Bromobenzoic acid | .04 g |

To prepare this medium, mix all the ingredients in the same sequence shown above except for P-Bromobenzoic acid. Stir on a magnetic stir plate until all ingredients are thoroughly dissolved which will take approximately 20 to 30 minutes. Dissolve the P-Bromobenzoic acid in 3 ml of 0.3 N sodium hydroxide and then pour this into the above solution. Adjust the pH to 6.8–7.5 using 1 N sodium hydroxide or 1 N hydrochloric acid. Filter sterilize the medium through a 0.45 micron filter.

As prepared the medium of the example is at ½ the usual concentration for use in the cells and cards described in U.S. Pat. No. 4,118,280 entitled "Automated Microbial Analyzer."

Thus there has been described a novel selective carbohydrate and a detection medium incorporating the same for detecting Salmonella spp. microorganisms which fulfills all of the objects and advantages sought therefore. Many changes, modifications, variations and other uses and applications of the subject invention will become apparent to those skilled in the art after considering the foregoing specification together with the accompanying claims. All such changes, modifications, variations and other uses and applications which do not depart from the spirit or scope of the invention are deemed to be covered by the invention which is limited only by the claims which follow.

What is claimed is:

1. A process of selectively differentiating Salmonella spp., Arizona spp., and some of the *Citrobacter freundii* from other members of the Enterobacteriaceae family in a liquid medium including adding 2-Deoxy-D-Ribose to the liquid medium as the carbohydrate source in an amount sufficient to differentiate Salmonella spp., Arizona spp., and some of the *Citrobacter freundii* from other members of the Enterobacteriaceae family.

2. The method of selectively differentiating Salmonella spp., Arizona spp., and some of the *Citrobacter freundii* from other members of the Enterobacteriaceae family in a sample by introducing 2-Deoxy-D-Ribose into the sample as a source of carbohydrate for the metabolic processes of Salmonella spp., Arizona spp., and some of the *Citrobacter freundii* and then determining whether or not the 2-Deoxy-D-Ribose has been metabolized; wherein the metabolization of 2-Deoxy-D-Ribose is an indication of the presence of Salmonella spp., Arizona spp., and some of the *Citrobacter freundii*.

3. A selective medium for Salmonella spp. and Arizona spp. including the following ingredients:

| | |
|---|---|
| 2-Deoxy-D-Ribose | .1 to 1.0 g% |
| Protein source | .05 to 2.0 g% |
| Combined pH indicator and gram positive inhibitor | .05 to 1.0 g% |
| Beef extract | .01–.5 g% |
| Ferris ammonium citrate | .005–.1 g% |
| Sodium thiosulfate | .005–2 g% |
| Ascorbic acid | .01–.4 g% |

-continued

| | |
|---|---|
| P-Bromabenzoic acid | .004–.08 g% |
| pH indicator | .5–5 ml% |

4. The selective medium defined in claim 3 wherein said *Citrobacter freundii* inhibitor are 0.01 to 0.4 g % ascorbic acid and 0.004 to 0.08 g % P-Bromobenzoic acid.

5. The selective medium defined in claim 3 wherein said protein source is Proteose Peptone #3.

6. The selective medium defined in claim 3 wherein said combined pH indicator and gram positive inhibitor is bile salts.

7. The selective medium defined in claim 6 wherein said bile salts is 0.05 to 1.0 g % Bile Salts Mixture.

8. The selective medium defined in claim 3 wherein said Salmonella spp. growth accelerator are:
0.005 to 2 g % sodium thiosulfate;
0.005 to 1 g % ferric ammonium citrate; and
0.01 to 0.5 g % beef extract, said sodium thiosulfate and ferric ammonium citrate selecting against Arizona spp.

9. The selective medium defined in claim 3 including oxygen remover wherein said oxygen remover is 0.01 to 0.6 g % thioglycollic acid, sodium salt.

10. The selective medium defined in claim 3 wherein said pH indicator is 0.5 to 5 ml % of 1% reduced aniline blue.

11. The selective medium defined in claim 3 further including up to 1.0 g % dipotassium phosphate as a pH buffer to prevent small erratic pH changes which might be due to conditions other than carbohydrate metabolism.

12. A selective medium for Salmonella spp. and Arizona spp. including the following ingredients in the following proportions:

| | |
|---|---|
| Water pH 6.8 to 7.5 | 95.0 ml |
| 2-Deoxy-D-Ribose | .5 g |
| Protein source | .5 g |
| Bile salts | .5 g |
| Thioglycollic acid, sodium salt | .3 g |
| Dipotassium phosphate | .1 g |
| Sodium chloride | .5 g |
| Beef extract | .1 g |
| Reduced aniline blue | 2.00 ml |
| Ascorbic acid | .3 g |
| P-Bromobenzoic acid | .04 g. |

13. The selective medium defined in claim 12 including the following ingredients in the following proportions to also select against Arizona spp.:
Ferric ammonium citrate: 0.04 g
Sodium thiosulfate: 0.05 g.

* * * * *

UNITED STATES PATENT OFFICE
CERTIFICATE OF CORRECTION

PATENT NO. : 4,279,995
DATED : 21 July 1981
INVENTOR(S) : Leodis V. Woods, et al It is certified that error appears in the above-identified patent and that said Letters Patent are hereby corrected as shown below:

Front page, left column, Code [73] "Assignee: McDonnell Douglas Corporation, Long Beach, Calif." should read --[73] Assignee: Vitek Systems, Inc., St. Louis, Missouri--.

Signed and Sealed this

Eighth Day of December 1981

[SEAL]

Attest:

Attesting Officer

GERALD J. MOSSINGHOFF
Commissioner of Patents and Trademarks